US010428168B2

(12) United States Patent
Osumi et al.

(10) Patent No.: US 10,428,168 B2
(45) Date of Patent: Oct. 1, 2019

(54) COMPOSITION FOR POLYMERIZATION, METHOD FOR PRODUCING SAME, COMPOSITION FOR A COATING CONTAINING COMPOSITION FOR POLYMERIZATION, METHOD FOR PRODUCING COMPOSITION FOR A COATING USING COMPOSITION FOR POLYMERIZATION, AND METHOD FOR PRODUCING COATING

(71) Applicant: FUJIFILM Corporation, Tokyo (JP)

(72) Inventors: Saki Osumi, Kanagawa (JP); Kiyotaka Fukagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/668,792

(22) Filed: Aug. 4, 2017

(65) Prior Publication Data

US 2017/0335041 A1 Nov. 23, 2017

Related U.S. Application Data

(63) Continuation of application No. PCT/JP2016/053991, filed on Feb. 10, 2016.

(30) Foreign Application Priority Data

Feb. 17, 2015 (JP) ................................ 2015-028179
Jul. 1, 2015 (JP) ................................ 2015-132555

(51) Int. Cl.

| | |
|---|---|
| ***C07C 309/14*** | (2006.01) |
| ***C08F 20/60*** | (2006.01) |
| ***C08F 220/28*** | (2006.01) |
| ***C08F 220/60*** | (2006.01) |
| ***C09D 4/00*** | (2006.01) |
| ***C09D 133/26*** | (2006.01) |

(52) U.S. Cl.

CPC .......... *C08F 220/60* (2013.01); *C07C 309/14* (2013.01); *C08F 20/60* (2013.01); *C08F 220/28* (2013.01); *C09D 4/00* (2013.01); *C09D 133/26* (2013.01); *C08F 2220/281* (2013.01); *C08F 2220/606* (2013.01)

(58) Field of Classification Search

CPC ...... C07C 309/14; C08F 220/60; C08F 20/60; C08F 220/28; C08F 2220/281; C08F 2220/606; C09D 133/26; C09D 4/00

See application file for complete search history.

(56) References Cited

U.S. PATENT DOCUMENTS

| | | | |
|---|---|---|---|
| 7,811,387 | B2 | 10/2010 | Scialla et al. |
| 2009/0306292 | A1 | 12/2009 | Bendejacq et al. |
| 2012/0052444 | A1 | 3/2012 | Iwai |

FOREIGN PATENT DOCUMENTS

| | | | |
|---|---|---|---|
| JP | 57-19735 | A | 2/1982 |
| JP | 59-73560 | A | 4/1984 |
| JP | 2009-528440 | A | 8/2009 |
| JP | 2010-47724 | A | 3/2010 |
| JP | 2011-37759 | A | 2/2011 |
| JP | 4691868 | B2 | 6/2011 |
| JP | 2011-245846 | A | 12/2011 |
| JP | 2012-72369 | A | 4/2012 |

OTHER PUBLICATIONS

Genck, W., "Make the Most of Antisolvent Crystallization, A Number of Factors Can Affect Solids' Formation", Chemical Processing, Nov. 8, 2010, https://www.chemicalprocessing.com/articles/2010/210/.*

Machine English Translation of JP 2010-047724, Hideki et al., Mar. 2010.*

International Search Report for PCT/JP2016/053991 dated May 17, 2016 [PCT/ISA/210].

International Preliminary Report on Patentability issued from the International Bureau in counterpart International Application No. PCT/JP2016/053991, dated Aug. 22, 2017.

Translation of Written Opinion, issued by International Searching Authority in corresponding International Application No. PCT/JP2016/053991, dated May 17, 2016.

Communication dated Feb. 2, 2018 from the European Patent Office in counterpart Application No. 16752379.4.

Communication dated Jul. 2, 2019, from the European Patent Office in counterpart European Application No. 16752379.4.

* cited by examiner

*Primary Examiner* — Patrick D Niland
(74) *Attorney, Agent, or Firm* — Sughrue Mion, PLLC

(57) ABSTRACT

A composition for polymerization, which can improve the storage stability in a high-temperature environment when a specific sulfobetaine monomer is stored as powder and can inhibit the discoloration of a cured film when the monomer is made into a cured film, and a method for producing the composition for polymerization; a composition for a coating containing the composition for polymerization, a method for producing the composition for a coating using the composition for polymerization, and a method for producing a coating; the composition for polymerization contains a monomer represented by formula (I) and water, in which the moisture content is equal to or higher than 3% by mass and less than 10% by mass (I)

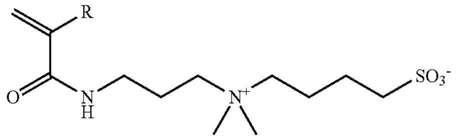

(R represents a hydrogen atom or a methyl group).

10 Claims, 1 Drawing Sheet

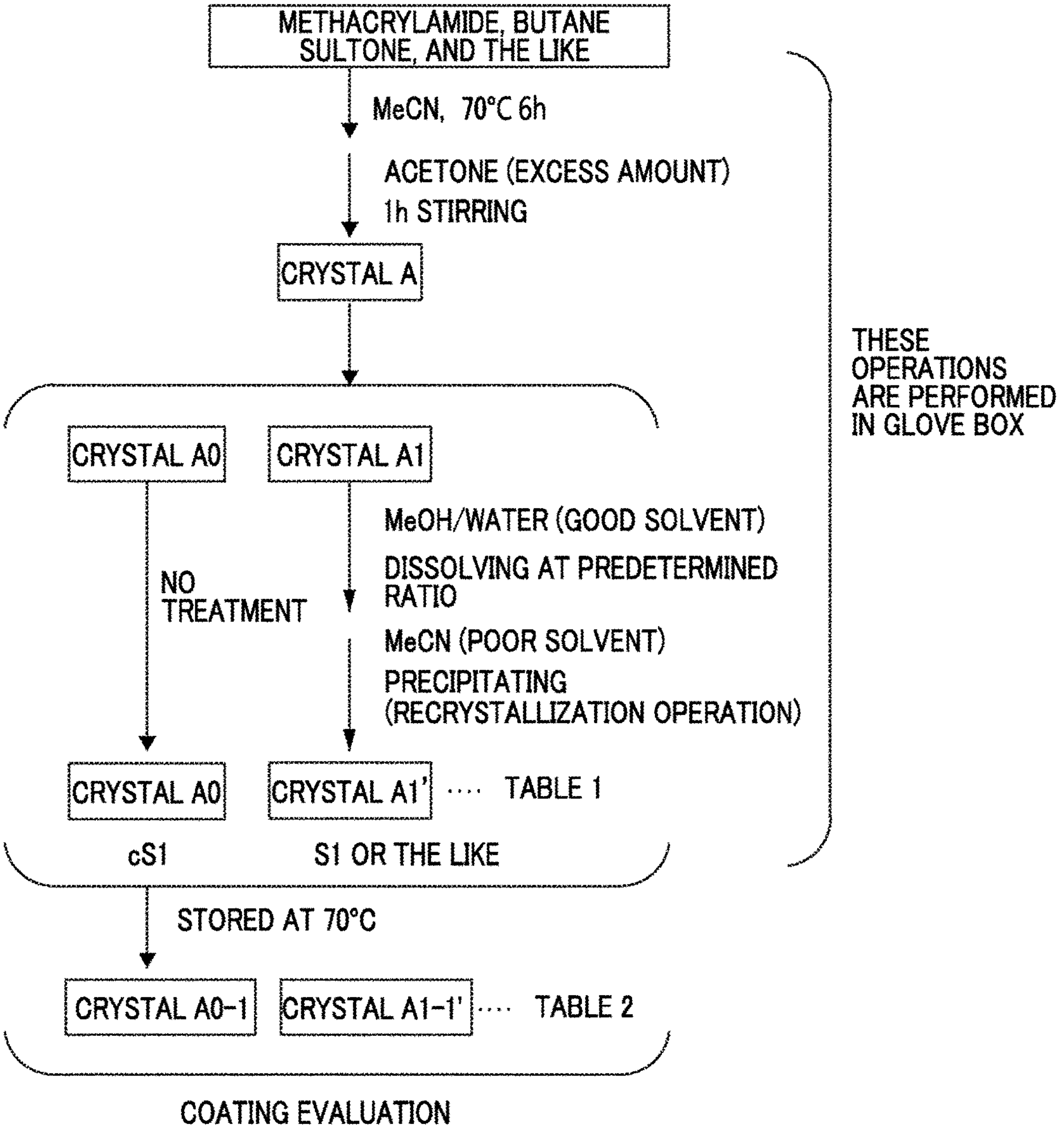
METHACRYLAMIDE, BUTANE SULTONE, AND THE LIKE
MeCN, 70°C 6h
ACETONE (EXCESS AMOUNT)
1h STIRRING
CRYSTAL A
THESE OPERATIONS ARE PERFORMED IN GLOVE BOX
CRYSTAL A0
CRYSTAL A1
MeOH/WATER (GOOD SOLVENT)
DISSOLVING AT PREDETERMINED RATIO
NO TREATMENT
MeCN (POOR SOLVENT)
PRECIPITATING (RECRYSTALLIZATION OPERATION)
CRYSTAL A0
CRYSTAL A1' ···· TABLE 1
cS1
S1 OR THE LIKE
STORED AT 70°C
CRYSTAL A0-1
CRYSTAL A1-1' ···· TABLE 2
COATING EVALUATION

COMPOSITION FOR POLYMERIZATION, METHOD FOR PRODUCING SAME, COMPOSITION FOR A COATING CONTAINING COMPOSITION FOR POLYMERIZATION, METHOD FOR PRODUCING COMPOSITION FOR A COATING USING COMPOSITION FOR POLYMERIZATION, AND METHOD FOR PRODUCING COATING

CROSS-REFERENCE TO RELATED APPLICATIONS

This application is a Continuation of PCT International Application No. PCT/JP2016/053991 filed on Feb. 10, 2016, which claims priority under 35 U.S.C. § 119 (a) to Japanese Patent Application No. 2015-028179 filed on Feb. 17, 2015, and to Japanese Patent Application No. 2015-132555 filed on Jul. 1, 2015. Each of the above applications is hereby expressly incorporated by reference, in its entirety, into the present application.

BACKGROUND OF THE INVENTION

1. Field of the Invention

The present invention relates to a composition for polymerization, a method for producing same, a composition for a coating containing the composition for polymerization, a method for producing a composition for a coating using the composition for polymerization, and a method for producing a coating.

2. Description of the Related Art

In the related art, taking advantage of their ionic bonding properties resulting from high hydrophilicity and its betaine structure, monomers having a betaine structure have been used for various industrial purposes. For example, the monomers have been used as a photographic sensitive material (JP1982-019735A (JP-S57-019735A)), a planographic printing plate (JP2011-245846A), an antifouling material (JP2009-528440A), a floor cleaning material (U.S. Pat. No. 7,811,387B), a biocompatible material (JP046918688), and a humectant for cosmetics (JP2011-037759A).

SUMMARY OF THE INVENTION

In the present invention, attention is paid particularly to a sulfobetaine monomer (hereinafter, referred to as a specific sulfobetaine monomer) having a structure of the following Formula (I).

(I)

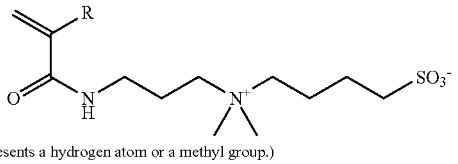

(R represents a hydrogen atom or a methyl group.)

This compound has high hydrophilicity and is expected to be widely used for various purposes described above. JP2011-245846A discloses a planographic printing plate precursor in which a polymer compound using this monomer is used as an undercoating agent, and describes that the use of the monomer makes it possible to simultaneously establish both of high stain resistance and printing durability. However, JP2011-245846A does not have a description or implication regarding the amount of moisture in the powder of the aforementioned specific sulfobetaine monomer. As a result of conducting research, the inventors of the present invention found that it is important to control the amount of moisture, and the control of the amount of moisture affects the storage stability when the monomer is used for various purposes described above.

Therefore, the present invention aims to provide a composition for polymerization, which makes it possible to improve the storage stability in a high-temperature environment when the specific sulfobetaine monomer is stored as powder and to inhibit the discoloration of a cured film when the monomer is made into a cured film, and a method for producing the composition for polymerization. Furthermore, the present invention aims to provide a composition for a coating containing the composition for polymerization, a method for producing a composition for a coating using the composition for polymerization, and a method for producing a coating.

According to the present invention, the following means are provided:

[1] A composition for polymerization, comprising a monomer represented by the following Formula (I) and water, in which a moisture content is equal to or higher than 3% by mass and less than 10% by mass, (I)

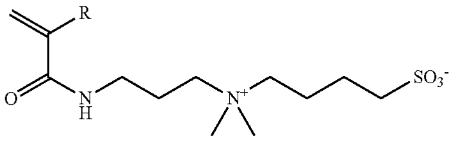

(R represents a hydrogen atom or a methyl group).

[2] The composition for polymerization described in [1], in which the moisture content is equal to or higher than 4% by mass and less than 9.5% by mass.

[3] The composition for polymerization described in [1] or [2], further comprising a monomer having an ethylenically unsaturated group.

[4] The composition for polymerization described in any one of [1] to [3], in which in the monomers, a content rate of the monomer represented by Formula (I) is equal to or higher than 5% by mass and equal to or less than 90% by mass.

[5] The composition for polymerization described in any one of [1] to [4] that is in a powdered state.

[6] The composition for polymerization described in any one of [1] to [5] that is obtained through steps of synthesizing the monomer represented by Formula (I), then adding the synthesized product to a good solvent, and subsequently mixing the good solvent with a poor solvent such that the monomer represented by Formula (I) is precipitated.

[7] A composition for a coating, comprising the composition for polymerization described in any one of [1] to [6] in a medium.

[8] The composition for a coating described in [7], in which the medium is an organic solvent.

[9] A composition for a coating, comprising a polymer compound obtained by polymerizing the monomer represented by Formula (I) contained in the composition described in [7] or [8].

[10] The composition for a coating described in [9], in which the polymer compound is further polymerized with a repeating unit derived from a monomer having an ethylenically unsaturated group.

[11] The composition for a coating described in [9] or [10], in which a content rate of a repeating unit derived from the monomer represented by Formula (I) in the polymer compound is equal to or higher than 5% and equal to or less than 90% based on mass.

[12] The composition for a coating described in any one of [7] to [11] that is in a liquid state.

[13] A method for producing a composition for a coating, comprising a step of mixing a composition for polymerization with a medium, in which the composition for polymerization contains a monomer represented by the following Formula (I) and water, and a moisture content in the composition for polymerization is equal to or higher than 3% by mass and less than 10% by mass,

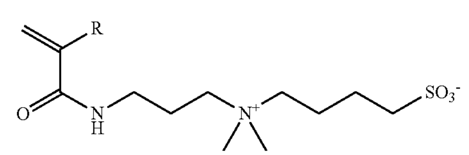

(I)

(R represents a hydrogen atom or a methyl group).

[14] The method for producing a composition for a coating described in [13], in which the composition for polymerization further contains a monomer having an ethylenically unsaturated group.

[15] A method for producing a coating, comprising steps of applying the composition for a coating obtained by the method for producing the composition for a coating described in [13] or [14] to a base material, polymerizing the monomer components contained in the composition such that a polymer compound is obtained, and forming a cured film of the polymer compound, or steps of polymerizing the monomer components contained in the composition for a coating obtained by the method for producing the composition for a coating described in [13] or [14] such that a polymer compound is obtained, and then applying the polymer compound to a base material such that a cured film of the polymer compound is formed.

[16] A method for producing a composition for polymerization that is for obtaining the composition for polymerization described in any one of [1] to [6], comprising steps of synthesizing the monomer represented by Formula (I), then adding the synthesized product to a good solvent, and subsequently mixing the good solvent with a poor solvent such that the monomer represented by Formula (I) is precipitated.

In the present specification, by definition, a coating includes a substance with which the surface of a base material is coated or covered, a substance inserted into the interface between base materials, and a substance embedded in voids. Typical examples of the coating include the substances with which the surface of cloth, paper, glass, or metals is coated. However, the coating is not limited to these substances, and includes the substances used as an adhesive or pressure sensitive adhesive of the aforementioned materials or used as a hole filler. The base material is not limited to those described above, and includes biomaterials (teeth or bones) and the like.

The composition for polymerization of the present invention contains the aforementioned specific sulfobetaine monomer. When the composition is stored in a powdered state, the composition demonstrates high storage stability in a high-temperature environment and can inhibit the discoloration of the formed cured film. Furthermore, according to the composition for a coating containing the composition for polymerization, the method for producing a composition for a coating using the composition for polymerization, and the method for producing a coating, it is possible to suitably provide products of stable quality having a coating. Furthermore, according to the method for producing a composition for polymerization of the present invention, it is possible to suitably produce a composition for polymerization having excellent properties described above.

The aforementioned characteristics, other characteristics, and advantages of the present invention may be further clarified by the following descriptions with reference to the appropriately attached drawings.

BRIEF DESCRIPTION OF THE DRAWING

FIG. 1 is a flowchart showing a procedure of preparing a composition for polymerization that was performed in examples.

DESCRIPTION OF THE PREFERRED EMBODIMENTS

The composition for polymerization of the present invention contains a specific sulfobetaine monomer and a specific amount of moisture. It is considered that, due to this constitution, the aforementioned excellent effects may be obtained for the following reasons for example, even though the reasons are unclear.

The specific sulfobetaine monomer of the present invention has a strong ionic intermolecular interaction resulting from the betaine structure in the molecule. Presumably, for this reason, the molecules may be close to each other in a crystal. It is considered that, when the monomer is stored at a high temperature, the closer the reactive moieties to each other inside the crystal, the easier it is for a reaction to occur which triggers the generation of a specific impurity.

In contrast, in a case of crystal containing water molecules within a specific range, the water molecules enter the voids of the crystal and play a role of causing charge relaxation for the betaine structure. Presumably, as a result, the aforementioned reaction of generating a specific impurity may be suppressed, and the monomer may be able to be stably stored even under a condition such as a high-temperature environment in which the reaction easily occurs. Meanwhile, by preventing the amount of moisture from increasing too much, the moisture which has not been incorporated into the crystal is not aggregated, and in this way, the composition of the present invention is inhibited from becoming a composition in which the monomer partially dissolves. It is considered that, accordingly, the motility of the monomers may not be excessively increased, and collision of the monomers may be prevented.

It is considered that the impurity generated when the composition is stored for a certain period of time in a high-temperature environment may perform an action of inducing a coating to be colored with the passage of time particularly when the composition is polymerized and made into a coating (cured film). It is considered that, in the coating (cured film) containing the specific impurity, a coloring component may be generated from the impurity component which has been generated when the composition is stored in a powdered state. It is considered that, in contrast, because the composition for polymerization of the present invention contains a specific amount of moisture, even if the composition is stored under a high-temperature condition, when the composition is made into a composition for a coating later, the coating may be inhibited or prevented from being colored with the passage of time.

[Specific Sulfobetaine Monomer]

The specific sulfobetaine monomer adopted in the present invention has a structure of the following Formula (I).

(I)

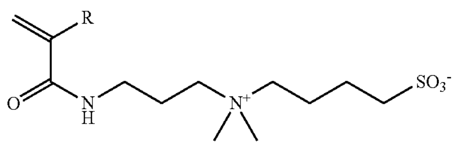

(R represents a hydrogen atom or a methyl group.)

The content rate of the specific sulfobetaine monomer in the composition for polymerization is not particularly limited, but is preferably equal to or higher than 5% by mass, more preferably equal to or higher than 10% by mass, and particularly preferably equal to or higher than 20% by mass in the monomer components (100% by mass) contained in the composition. The upper limit of the content rate may be 100% by mass. In a case where the other monomers are added to the composition, the upper limit is preferably equal to or less than 95% by mass, more preferably equal to or less than 90% by mass, and particularly preferably equal to or less than 80% by mass. The ratio is a copolymerization ratio at the time of making the sulfobetaine monomer into a polymer compound which will be described later. One kind of the specific sulfobetaine monomer may be used, or two kinds thereof may be used by being mixed together.

The specific sulfobetaine monomer can be synthesized by a common method. For example, the synthesis examples or example compounds described in JP2011-245846A, JP2012-187907A, JP2012-31400A, and the like can be referred to. Specifically, by reacting a predetermined polyamine compound with a (meth)acrylic acid chloride compound, an amino group-containing (meth)acrylamide compound is obtained. By reacting the amino group-containing (meth)acrylamide compound with a sultone compound having a predetermined number of carbon atoms, a compound having a sulfobetaine structure can be obtained. Specifically, for example, the description of paragraphs [0189] to [0193] of JP2012-31400A and the like can be referred to.

[Moisture]

The moisture contained in the composition for polymerization of the present invention is not particularly limited. The moisture may be contained in the composition by being incorporated into the crystal structure of the aforementioned monomer component or by being coordinated with the monomer molecule. Here, the amount of moisture is relatively stable, and in an embodiment of the present invention, the amount of moisture does not dramatically change in the air at room temperature. However, the present invention is not limited to the embodiment.

The content rate of moisture in the composition for polymerization is equal to or higher than 3% by mass with respect to the total amount of the composition, and is preferably equal to or higher than 4% by mass. The upper limit thereof is generally less than 10% by mass and is preferably less than 9.5% by mass. In the present invention, it is important to control the amount of moisture within the aforementioned range. By controlling the amount of moisture within the above range, it is possible to obtain storage stability over time through the action described above and to inhibit or prevent the discoloration of a coating film.

The amount of moisture in the composition for polymerization may be controlled by any method. For example, it is possible to control the amount of moisture by varying the moisture content of a reaction medium or a purification solvent (alcohol compound or the like) used at the time of synthesizing the specific sulfobetaine monomer. Specifically, by increasing the moisture content of an alcohol (methanol or the like) used at the time of reacting the aforementioned amino group-containing (meth)acrylamide compound with a sultone compound or the moisture content of a solvent used in a purification operation following the reaction, or by performing the reaction operation in a high-humidity environment, the moisture content in the formed composition for polymerization (powder) can be increased.

Hereinafter, an example of the aforementioned purification operation will be described. FIG. 1 is a flowchart illustrating an example of the purification operation including the relationship with examples which will be described later. A crystal A is obtained by a common method based on JP2011-245846A or the like. The crystal A which is directly adopted as a crystal A0 sample without being treated is cS1 which will be a comparative example that will be described later. Meanwhile, by separating the crystal A as a crystal A1, dissolving the crystal A1 in a good solvent, and mixing the good solvent with a poor solvent such that recrystallization occurs, a desired crystal A1' is prepared. Among crystals A1', the crystal in which the amount of moisture is within a predetermined range becomes an example. The amount of moisture is adjusted by the concentration of water in the good solvent and the like as described above. Alternatively, for example, it is possible to use a method of using water as a good solvent and drying the water as it is, although the method is not illustrated in the drawing.

In the present specification, “good solvent” means a solvent which can dissolve the composition for polymerization (powder), and is preferably a solvent in which the composition for polymerization has a solubility equal to or higher than 10% in terms of mass at a temperature of 25° C. Specific examples of the good solvent include a sulfoxide compound (dimethyl sulfoxide), an alcohol compound (ethanol, methanol, or the like), and water. In contrast, “poor solvent” means a solvent in which the composition for polymerization (powder) does not dissolve or poorly dissolves, and is preferably a solvent in which the composition for polymerization has a solubility of less than 0.5% in terms of mass at a temperature of 25° C. Specific examples of the poor solvent include a ketone compound (acetone or the like), a nitrile compound (acetonitrile or the like), an ester compound (ethyl acetate or the like), a hydrocarbon compound (hexane, toluene, or the like), and the like.

[Copolymerization Component]

In the present invention, the composition for polymerization may contain, as monomer components, only the specific sulfobetaine monomer or other monomer components. Examples of copolymerizable monomers include monomers having an ethylenically unsaturated bond (ethylenic monomers) such as (meth)acrylic acid esters (acrylic acid esters or methacrylic acid esters) including methyl (meth)acrylate, ethyl (meth)acrylate, n-butyl (meth)acrylate, 2-ethylhexyl (meth)acrylate, 2-hydroxyethyl (meth)acrylate, 2-hydroxypropyl (meth)acrylate, 3-(meth)acryloyloxypropyl sulfonate, N,N-dimethylaminoethyl (meth)acrylate, N,N-diethylaminoethyl (meth)acrylate, polyalkylene glycol mono (meth)acrylate, polyalkylene glycol di(meth)acrylate, and 2-(meth)acryloyloxyethyl methyl sulfoxide.

Examples of the copolymerizable monomers also include a carboxyl group-containing ethylenic monomer such as (meth)acrylic acid (acrylic acid or methacrylic acid), crotonic acid, or itaconic acid, the polymerizable compounds 1 to 12 described in paragraph [0031] in Journal of Technical Disclosure No. 2013-502654, the polyfunctional compounds 1 to 11 described in paragraph [0192] in Journal of Technical Disclosure No. 2013-502654, N-(2-acetamidoethyl)-N-(2-hydroxyethyl)acrylamide, and the like. The examples also include a monomer obtained by modifying one terminal or both terminals of polyalkylene glycol (polyethylene glycol or the like). Examples of the terminal group include a vinyl group, an allyl group, a (meth)acryloyl group, and the like.

The examples also include various ethylenic monomers such as styrene, vinyl chloride, acrylonitrile, vinylpyridine, vinylpyrrolidone, and p-styrenesulfonate and (meth)acrylamide monomers such as (meth)acrylamide and (meth) acrylamide-2-methyl-propanesulfonate.

Among these, a (meth)acrylic acid alkyl ester monomer is preferable (the number of carbon atoms other than the (meth)acryloyl group is preferably 1 to 12, more preferably 1 to 6, and particularly preferably 2 to 4). The alkyl ester moiety may have a substituent T. For example, the alkyl ester moiety may have a hydroxyl group and/or a carboxyl group and the like. Alternatively, an oxygen atom may be contained in the alkyl chain. Particularly, 2-hydroxyethyl (meth)acrylate, n-butyl (meth)acrylate, tetraethylene glycol di(meth)acrylate, and the like are preferable.

In the present specification, when a group is referred to as "acryl" or "acryloyl", the group includes not only an acryloyl group but also a wide variety of groups including a derivative structure thereof as well as a structure having a specific substituent in the α-position of the acryloyl group. Here, in a narrow sense, the group having a hydrogen atom in the α-position is referred to as acryl or acryloyl in some cases. The group having a methyl group in the α-position is referred to as methacryl, and any of acryl (having a hydrogen atom in the α-position) and methacryl (having a methyl group in the α-position) is referred to as (meth)acryl or the like in some cases.

The number of ethylenically unsaturated bonds in the molecule of the ethylenic monomer is not particularly limited, but is preferably 1 to 8, more preferably 1 to 4, and particularly preferably 1 or 2.

As monomers constituting the copolymerization components, compounds represented by the following formulae are also preferable.

(M-1)

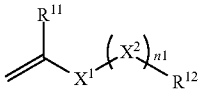

-continued (M-2)

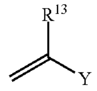

$R^{11}$ and $R^{13}$ each independently represent a hydrogen atom, an alkyl group (preferably having 1 to 12 carbon atoms, more preferably having 1 to 6 carbon atoms, and particularly preferably having 1 to 3 carbon atoms), a hydroxyl group, a cyano group, or a halogen atom.

Among these, a hydrogen atom or a methyl group is preferable.

$X^1$ represents a single bond or a linking group. As the linking group, a hetero linking group as a linking group La which will be described later is preferable, and CO, O, S, $NR^N$, or a combination of these is more preferable. $R^N$ has the same definition as a group which will be defined later. $X^1$ is even more preferably COO or $CONR^N$ among the above.

$X^2$ represents a linking group, and is preferably a hydrocarbon linking group as the linking group La which will be described later. Examples of the linking group include linking groups having a polymer or oligomer structure of the linking group La. Specific examples thereof include a (poly) alkyleneoxy group, a carbonyl (poly)oxyalkylene group, a carbonyl (poly)alkyleneoxy group, a carbonyloxy(poly) alkyleneoxy group, a (poly)alkyleneimino group, an alkylene (poly)iminoalkylene group, a carbonyl (poly)iminoalkylene group, a carbonyl (poly)alkyleneimino group, a (poly)ester group, and a (poly)amide group. At this time, the number x of repeating units is preferably within the same range as will be described later, more preferably 1 to 20, and even more preferably 1 to 10. When $X^2$ represents a group which can have a substituent, $X^2$ may further have the substituent T. Examples of the substituent that $X^2$ may further have include a hydroxyl group, a cyano group, a halogen atom, an alkoxy group, an acyl group, a carboxyl group (or a salt or ester thereof), a sulfonic acid group (or a salt or ester thereof), a phosphoric acid group (or a salt or ester thereof), and a phosphonic acid group (or a salt or ester thereof).

Examples of $R^{12}$ include hydrogen atom or the substituent T. Among these, a hydrogen atom, a hydroxyl group, a halogen atom, an alkoxy group, an acyl group, an alkyl group, an alkenyl group, a (meth)acryloyl group, a (meth) acryloyloxy group, and a (meth)acryloylimino group are preferable. When $R^{12}$ is a group which can have a substituent, $R^{12}$ may further have the substituent T. Examples of the substituent that $R^{12}$ may further have include a hydroxyl group, a cyano group, a halogen atom, an alkoxy group, an acyl group, a carboxyl group (or a salt or ester thereof), a sulfonic acid group (or a salt or ester thereof), a phosphoric acid group (or a salt or ester thereof), and a phosphonic acid group (or a salt or ester thereof).

Examples of Y include an alkyl group (preferably having 1 to 12 carbon atoms, more preferably having 1 to 6 carbon atoms, and particularly preferably having 1 to 3 carbon atoms), an alkenyl group (preferably having 2 to 12 carbon atoms and more preferably having 2 to 6 carbon atoms), an alkynyl group (preferably having 2 to 12 carbon atoms and more preferably having 2 to 6 carbon atoms), an aryl group (preferably having 6 to 22 carbon atoms, more preferably having 6 to 14 carbon atoms, and particularly preferably having 6 to 10 carbon atoms), an aralkyl group (preferably having 7 to 23 carbon atoms, more preferably having 7 to 15 carbon atoms, and particularly preferably having 7 to 11 carbon atoms), a heteroaryl group, and a cyano group. Examples of the heteroaryl group include those exemplified above for the heterocyclic group of the substituent T. Among these, a pyrrolidone group can be exemplified. When Y is a group which can have a substituent, Y may further have the substituent T. Examples of the substituent that Y may further have include a hydroxyl group, a cyano group, a halogen atom, an alkoxy group, an acyl group, a carboxyl group (or a salt or ester thereof), a sulfonic acid group (or a salt or ester thereof), a phosphoric acid group (or a salt or ester thereof), and a phosphonic acid group (or a salt or ester thereof).

n1 is 0 or 1.

Regarding the description of a compound (for example, in a case where "compound" or "monomer" is used as a suffix) in the present specification, the compound includes not only the compound itself but also a salt and ion thereof. Furthermore, as long as a desired effect is obtained, the compound includes derivatives obtained by partial modification such as introduction of a substituent.

In the present specification, in a case where there is no clear description regarding whether a substituent is substituted or unsubstituted, as long as a desired effect is obtained, the substituent may have any substituent (the same shall be applied to a linking group). The same shall be applied to a compound which is not clearly described regarding whether the compound is substituted or unsubstituted. Examples of the preferred substituents include the following substituent T.

Examples of the substituent T include the following groups.

Examples of the substituent T include an alkyl group (preferably an alkyl group having 1 to 20 carbon atoms, such as methyl, ethyl, isopropyl, t-butyl, pentyl, heptyl, 1-ethylpentyl, benzyl, 2-ethoxyethyl, or 1-carboxymethyl), an alkenyl group (preferably an alkenyl group having 2 to 20 carbon atoms, such as vinyl, allyl, or oleyl), an alkynyl group (preferably an alkynyl group having 2 to 20 carbon atoms, such as ethynyl, butadienyl, or phenylethynyl), a cycloalkyl group (preferably a cycloalkyl group having 3 to 20 carbon atoms, such as cyclopropyl, cyclopentyl, cyclohexyl, or 4-methylcyclohexyl), an aryl group (preferably an aryl group having 6 to 26 carbon atoms, such as phenyl, 1-naphthyl, 4-methoxyphenyl, 2-chlorophenyl, or 3-methylphenyl), a heterocyclic group (preferably a heterocyclic group having 2 to 20 carbon atoms and a 5- or 6-membered heterocyclic group containing at least one oxygen atom, sulfur atom, or nitrogen atom, such as a tetrahydropyran, tetrahydrofuran, 2-pyridyl, 4-pyridyl, 2-imidazolyl, 2-benzimidazolyl, 2-thiazolyl, 2-oxazolyl, or pyrrolidone group), an alkoxy group (preferably an alkoxy group having 1 to 20 carbon atoms, such as methoxy, ethoxy, isopropyloxy, or benzyloxy), an aryloxy group (preferably an aryloxy group having 6 to 26 carbon atoms, such as phenoxy, 1-naphthyloxy, 3-methylphenoxy, or 4-methoxyphenoxy), an alkoxycarbonyl group (preferably an alkoxycarbonyl group having 2 to 20 carbon atoms, such as ethoxycarbonyl or 2-ethylhexyloxycarbonyl), an aryloxycarbonyl group (preferably an aryloxycarbonyl group having 6 to 26 carbon atoms, such as phenoxycarbonyl, 1-naphthyloxycarbonyl, 3-methylphenoxycarbonyl, or 4-methoxyphenoxycarbonyl), an amino group (preferably an amino group having 0 to 20 carbon atoms including an alkylamino group or an arylamino group, such as amino, N,N-dimethylamino, N,N-diethylamino, N-ethylamino, or anilino), a sulfamoyl group (preferably a sulfamoyl group having 0 to 20 carbon atoms, such as N,N-dimethylsulfamoyl or N-phenylsulfamoyl), an acyl group (preferably an acyl group having 1 to 20 carbon atoms, such as acetyl, propionyl, or butyryl), an aryloyl group (preferably an aryloyl group having 7 to 23 carbon atoms, such as benzoyl), an acyloxy group (preferably an acyloxy group having 1 to 20 carbon atoms, such as acetyloxy), an aryloyloxy group (preferably an aryloyloxy group having 7 to 23 carbon atoms, such as benzoyloxy), a carbamoyl group (preferably a carbamoyl group having 1 to 20 carbon atoms, such as N,N-dimethylcarbamoyl or N-phenylcarbamoyl), an acylamino group (preferably an acylamino group having 1 to 20 carbon atoms, such as acetylamino or benzoylamino), an alkylthio group (preferably an alkylthio group having 1 to 20 carbon atoms, such as methylthio, ethylthio, isopropylthio, or benzylthio), an arylthio group (preferably an arylthio group having 6 to 26 carbon atoms, such as phenylthio, 1-naphthylthio, 3-methylphenylthio, or 4-methoxyphenylthio), an alkylsulfonyl group (preferably an alkylsulfonyl group having 1 to 20 carbon atoms, such as methylsulfonyl or ethylsulfonyl), an arylsulfonyl group (preferably an arylsulfonyl group having 6 to 22 carbon atoms, such as benzenesulfonyl), an alkylsilyl group (preferably an alkylsilyl group having 1 to 20 carbon atoms, such as monomethylsilyl, dimethylsilyl, trimethylsilyl, or triethylsilyl), an arylsilyl group (preferably an arylsilyl group having 6 to 42 carbon atoms, such as triphenylsilyl), a phosphoryl group (preferably a phosphoryl group having 0 to 20 carbon atoms, such as $—OP(=O)(R^P)_2$), a phosphonyl group (preferably a phosphonyl group having 0 to 20 carbon atoms, such as $—P(=O)(R^P)_2$), a phosphinyl group (preferably a phosphinyl group having 0 to 20 carbon atoms, such as $—P(R^P)_2$), a (meth)acryloyl group, a (meth)acryloyloxy group, a (meth)acryloylimino group ((meth)acrylamide group), a hydroxyl group, a thiol group, a carboxyl group, a phosphoric acid group, a phosphonic acid group, a sulfonic acid group, a cyano group, and a halogen atom (such as a fluorine atom, a chlorine atom, a bromine atom, or an iodine atom).

Each of the groups exemplified as the substituent T may be further substituted with the substituent T.

When the aforementioned substituent is an acidic group or a basic group, the substituent may form a salt thereof.

When the compound, the substituent, the linking group, or the like contains an alkyl group or an alkylene group, an alkenyl group or an alkenylene group, an alkynyl group or an alkynylene group, and the like, these may be cyclic or chain-like, may be linear or branched, or may be substituted as described above or unsubstituted.

As long as the effects of the present invention are obtained, each substituent specified in the present specification may be substituted through the following linking group La, or the linking group La may be contained in the structure of the substituent. For example, an alkyl group or an alkylene group, an alkenyl group or an alkenylene group, and the like may additionally contain the following hetero linking group in the structure thereof.

As the linking group La, a hydrocarbon linking group [an alkylene group having 1 to 10 carbon atoms (more preferably having 1 to 6 carbon atoms and even more preferably having 1 to 3 carbon atoms), an alkenylene group having 2 to 10 carbon atoms (more preferably having 2 to 6 carbon atoms and even more preferably having 2 to 4 carbon atoms), an alkynylene group having 2 to 10 carbon atoms (more preferably having 2 to 6 carbon atoms and even more preferably having 2 to 4 carbon atoms), an arylene group having 6 to 22 carbon atoms (more preferably having 6 to 10 carbon atoms), or a combination of these], a hetero linking group [a carbonyl group (—CO—), a thiocarbonyl group (—CS—), an ether group (—O—), a thioether group (—S—), an imino group (—$NR^N$—), an imine linking group ($R^N$—N═C< or —N═C($R^N$)—), a sulfonyl group (—$SO_2$—), a sulfinyl group (—SO—), a phosphoric acid linking group (—O—P(OH)(O)—O—), a phosphonic acid linking group (—P(OH)(O)—O—), or a combination of these], or a linking group obtained by combining these is preferable. In a case of a ring formed by condensation, the aforementioned hydrocarbon linking group may be linked by appropriately forming a double bond or a triple bond. The formed ring is preferably a 5- or 6-membered ring. The 5-membered ring is preferably a nitrogen-containing 5-membered ring, and examples of compounds forming such a ring include pyrrole, imidazole, pyrazol, indazole, indole, benzimidazole, pyrrolidine, imidazolidine, pyrazolidine, indoline, carbazole, derivatives of these, and the like. Examples of the 6-membered ring include piperidine, morpholine, piperazine, derivatives of these, and the like. When the ring contains an aryl group, a heterocyclic group, and the like, these may be a monocyclic ring or a condensed ring and may be substituted or unsubstituted.

$R^N$ is a hydrogen atom or a substituent. As the substituent, an alkyl group (preferably having 1 to 24 carbon atoms, more preferably having 1 to 12 carbon atoms, even more preferably having 1 to 6 carbon atoms, and particularly preferably having 1 to 3 carbon atoms), an alkenyl group (preferably having 2 to 24 carbon atoms, more preferably having 2 to 12 carbon atoms, even more preferably having 2 to 6 carbon atoms, and particularly preferably having 2 or 3 carbon atoms), an alkynyl group (preferably having 2 to 24 carbon atoms, more preferably having 2 to 12 carbon atoms, even more preferably having 2 to 6 carbon atoms, and particularly preferably having 2 or 3 carbon atoms), an aralkyl group (preferably having 7 to 22 carbon atoms, more preferably having 7 to 14 carbon atoms, and particularly preferably having 7 to 10 carbon atoms), and an aryl group (preferably having 6 to 22 carbon atoms, more preferably having 6 to 14 carbon atoms, and particularly preferably having 6 to 10 carbon atoms) are preferable.

$R^P$ is a hydrogen atom, a hydroxyl group, or a substituent. As the substituent, an alkyl group (preferably having 1 to 24 carbon atoms, more preferably having 1 to 12 carbon atoms, even more preferably having 1 to 6 carbon atoms, and particularly preferably having 1 to 3 carbon atoms), an alkenyl group (preferably having 2 to 24 carbon atoms, more preferably having 2 to 12 carbon atoms, even more preferably having 2 to 6 carbon atoms, and particularly preferably having 2 or 3 carbon atoms), an alkynyl group (preferably having 2 to 24 carbon atoms, more preferably having 2 to 12 carbon atoms, even more preferably having 2 to 6 carbon atoms, and particularly preferably having 2 or 3 carbon atoms), an aralkyl group (preferably having 7 to 22 carbon atoms, more preferably having 7 to 14 carbon atoms, and particularly preferably having 7 to 10 carbon atoms), an aryl group (preferably having 6 to 22 carbon atoms, more preferably having 6 to 14 carbon atoms, and particularly preferably having 6 to 10 carbon atoms), an alkoxy group (preferably having 1 to 24 carbon atoms, more preferably having 1 to 12 carbon atoms, even more preferably having 1 to 6 carbon atoms, and particularly preferably having 1 to 3 carbon atoms), an alkenyloxy group (preferably having 2 to 24 carbon atoms, more preferably having 2 to 12 carbon atoms, even more preferably having 2 to 6 carbon atoms, and particularly preferably having 2 or 3 carbon atoms), an alkynyloxy group (preferably having 2 to 24 carbon atoms, more preferably having 2 to 12 carbon atoms, even more preferably having 2 to 6 carbon atoms, and particularly preferably having 2 or 3 carbon atoms), an aralkyloxy group (preferably having 7 to 22 carbon atoms, more preferably having 7 to 14 carbon atoms, and particularly preferably having 7 to 10 carbon atoms), and an aryloxy group (preferably having 6 to 22 carbon atoms, more preferably having 6 to 14 carbon atoms, and particularly preferably having 6 to 10 carbon atoms) are preferable.

In the present specification, the number of atoms constituting the linking group is preferably 1 to 36, more preferably 1 to 24, even more preferably 1 to 12, and particularly preferably 1 to 6. The number of linking atoms in the linking group is preferably equal to or less than 10 and more preferably equal to or less than 8. The lower limit of the number of linking atoms is equal to or greater than 1. The number of linking atoms refers to the minimum number of atoms which are positioned in a path connecting the predetermined structural portions to each other and are involved in linking. For example, in a case of —$CH_2$—C(═O)—O—, while the number of atoms constituting the linking group is 6, the number of linking atoms is 3.

Specific examples of combinations of the linking groups include an oxycarbonyl group (—OCO—), a carbonate group (—OCOO—), an amide group (—CONH—), a urethane group (—NHCOO—), a urea group (—NHCONH—), a (poly)alkyleneoxy group (—(Lr—O)x-), a carbonyl (poly)oxyalkylene group (—CO—(O—Lr)x-), a carbonyl (poly)alkyleneoxy group (—CO—(Lr—O)x-), a carbonyloxy (poly)alkyleneoxy group (—COO—(Lr—O)x-), a (poly)alkyleneimino group (—(Lr—$NR^N$)x-), an alkylene (poly)iminoalkylene group (—Lr—(NR—Lr)x-), a carbonyl (poly)iminoalkylene group (—CO—($NR^N$—Lr)x-), a carbonyl (poly)alkyleneimino group (—CO—(Lr—$NR^N$)x-), a (poly)ester group (—(CO—O—Lr)x-, —(O—CO—Lr)x-, —(Lr—CO—O)x-, or —(Lr—O—CO)x-), a (poly)amide group (—(CO—$NR^N$—Lr)x-, —($NR^N$—CO—Lr)x-, —($NR^N$—Lr—CO)x-, —(Lr—CO—$NR^N$)x-, or —(Lr—$NR^N$—CO)x-), and the like, x is an integer equal to or greater than 1, x is preferably 1 to 500, and more preferably 1 to 100.

Lr is preferably an alkylene group, an alkenylene group, or an alkynylene group. The number of carbon atoms in Lr is preferably 1 to 12, more preferably 1 to 6, and particularly preferably 1 to 3. A plurality of Lr's, $R^N$'s, R's, x's, and the like do not need to be the same as each other. The orientation of the linking group is not limited to the above description, and may be appropriately understood as the orientation matching with a predetermined chemical formula.

[Producing Method]

Any method may be used for reacting the composition for polymerization of the present invention so as to polymerize the monomer contained in the composition. For example, by reacting the specific sulfobetaine monomer with a monomer which is used as necessary to constitute copolymerization components in a solvent in the presence of a polymerization initiator, a polymer is obtained (hereinafter, the polymer will be referred to as a polymer compound (A) in some cases). The solvent used herein only needs to dissolve each of the monomers. Specific examples of the solvent include water, methanol, ethanol, propanol, t-butanol, benzene, toluene, dimethylformamide, tetrahydrofuran, chloroform, a mixed solvent of these, and the like. As the polymerization initiator, any of the general radical initiators may be used. Examples of the polymerization initiator include an azo compound such as 2,2'-azobisisobutyronitrile (AIBN), 3-carboxypropionitrile, azobismalenonitrile, or dimethyl-(2,2')-azobis(2-methylpropionate), an organic peroxide such as benzoyl peroxide, lauroyl peroxide, or potassium persulfate, a 1:1 (mass ratio) mixture of 1-hydroxy-cyclohexyl-phenyl-ketone and benzophenone, and an alkylphenone-based compound such as 2-hydroxy-2-methyl-1-phenyl-propan-1-one, 1-[4-(2-hydroxyethoxy)-phenyl]-2-hydroxy-2-methyl-1-propan-1-one, or 2-hydroxy-1-(4-(2-(2-hydroxyethoxy)ethoxy)phenyl)-2-methylpropan-1-one. In the present invention, the reaction solvent and the polymerization initiator used for the aforementioned polymerization reaction are not limited to the above. Furthermore, if necessary, other additives such as a polymerization inhibitor may be used.

(Ia)

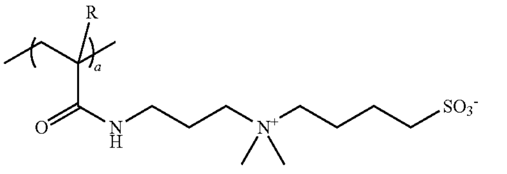

(M-1a)

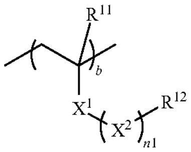

(M-2a)

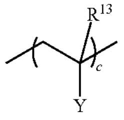

If the polymer compound (A) is described using a structural formula, the compound is preferably a compound having a repeating unit of the above Formula (Ia). At the time of making a copolymer, the compound is more preferably a compound additionally having a repeating unit of Formula (M-1a) and/or a repeating unit of Formula (M-2a). In the formulae, R, $R^{11}$ to $R^{13}$, $X^1$, $X^2$, Y, and n1 each have the same definition as R, $R^{11}$ to $R^{13}$, $X^1$, $X^2$, Y, and n1 in each of Formulae (I), (M-1), and (M-2). Regarding the copolymerization ratios a, b, and c, provided that the sum of a, b, and c equals 100% based on mass, a is preferably equal to or higher than 5% by mass, more preferably equal to or higher than 10% by mass, and particularly preferably equal to or higher than 20% by mass. The upper limit may be 100% by mass. At the time of making a copolymer, a is preferably equal to or less than 95% by mass, more preferably equal to or less than 90% by mass, and particularly preferably equal to or less than 80% by mass. Each of b and c may be equal to or higher than 0% by mass. Each of b and c is preferably equal to or higher than 10% by mass, and particularly preferably equal to or higher than 20% by mass. The upper limit of b and c is preferably equal to or less than 90% by mass, and more preferably equal to or less than 80% by mass.

[Molecular Weight]

The weight-average molecular weight of the polymer compound (A) can be variously adjusted according to the purpose of use thereof. The weight-average molecular weight is preferably equal to or greater than 5,000, and more preferably equal to or greater than 10,000. The upper limit thereof is preferably equal to or less than 1,000,000, more preferably equal to or less than 5,000.000, and even more preferably equal to or less than 2,000,000. In a case where the polymer compound (A) is made into a low-molecular weight compound, the weight-average molecular weight is preferably equal to or less than 500,000, more preferably equal to or less than 200,000, and even more preferably equal to or less than 100,000. In a case where the weight-average molecular weight of the polymer compound (A) is too small, this is not preferable in view of producing in some cases because it is difficult to control the molecular weight. In a case where the weight-average molecular weight of the polymer compound (A) is too big, in some cases, a desired performance is not demonstrated, or it is difficult to produce the compound because the viscosity is too high.

In the present invention, unless otherwise specified, the molecular weight of a polymer compound (polymer or oligomer) refers to a weight-average molecular weight, and a value measured by gel permeation chromatography (GPC) and expressed in terms of standard polystyrene is adopted. Basically, the measurement device and the measurement conditions are based on the following condition 1, and depending on the solubility of a sample or the like, the condition 2 may be acceptable. Here, depending on the polymer species, an appropriate carrier (eluent) and a column compatible with the carrier may be selected and used. For other details. JIS K 7252-1 to 4:2008 may be referred to. For a poorly soluble polymer compound, the weight-average molecular weight is measured under the following conditions at a concentration at which the compound can be dissolved.

(Condition 1)

Column: a column obtained by connecting TOSOH TSKgel Super HZM-H, TOSOH TSKgel Super HZ4000, and TOSOH TSKgel Super HZ2000 is used.

Carrier: tetrahydrofuran

Measurement temperature: 40° C.

Flow rate of carrier, 1.0 ml/min

Sample concentration: 0.1% by mass

Detector: refractive index (RI) detector

Injection amount: 0.1 ml (Condition 2)

Column: two columns of TOSOH TSKgel Super AWM-H are connected.

Carrier: 10 mM LiBr/N-methylpyrrolidone Measurement temperature: 40° C.

Flow rate of carrier: 1.0 ml/min

Sample concentration: 0.1% by mass

Detector: refractive index (RI) detector

Injection amount: 0.1 ml

[Composition for Coating]

The composition for a coating according to the present invention can be produced by mixing the composition for polymerization, which contains the specific sulfobetaine monomer and water, with a medium. At this time, a copolymerization component such as an ethylenically unsaturated group-containing monomer may be further added thereto. The method for forming a coating (cured film) by using the composition for a coating is not particularly limited. For example, it is possible to use a method in which the composition for a coating is applied to a base material, and the monomer components contained in the composition for a coating are polymerized such that a cured film of the polymer compound (A) is formed. Alternatively, a method may be used in which first, the monomer components contained in the composition for a coating are polymerized such that the polymer compound (A) is obtained, the compound is then applied to a base material, and a cured film of the polymer compound is formed by drying or the like.

The concentration of the polymer compound (A) in the composition for a coating is preferably 0.1% to 20% by mass, and more preferably 0.1% to 10% by mass. It is preferable that the concentration of the polymer compound (A) is within the above range, because then excellent coating properties can be imparted.

Depending on the desired characteristics, the composition for a coating may contain one or more kinds of components selected from the group consisting of a polymer compound, an epoxy resin, an acryl resin, a surfactant, an antistatic agent, a coupling agent, and an epoxy curing agent and additives such as a pH adjuster, a rust inhibitor, a preservative, a fungicide, an antioxidant, an anti-reducing agent, an evaporation accelerator, a chelating agent, a water-soluble polymer, a pigment, a dye, a wettability enhancer, and a defoamer.

Examples of the polymer compound include polyamic acid, soluble polyimide, polyamide, polyamide imide, polyamic acid ester, polyester, an acrylic acid polymer, an acrylate polymer, polyvinyl alcohol, and polyoxyethylene. As the polymer compound, polyamic acid and a polyimide-based polymer compound such as soluble polyimide are preferable. The weight-average molecular weight of the polymer compound is preferably 1,000 to 10,000. In a case where the weight-average molecular weight is within this range, the solubility of the polymer compound in a solvent becomes excellent, and the polymer compound is preferable as a component contained in the composition for a coating. From the viewpoint of the solubility in a solvent, the weight-average molecular weight of the polymer compound is more preferably 1.000 to 7,500, even more preferably 1,000 to 5,000, and particularly preferably 1,000 to 2,000. In a case where the weight-average molecular weight is equal to or greater than 1,000, the polymer compound does not evaporate by a heating treatment and becomes chemically or mechanically stable. In a case where the weight-average molecular weight is equal to or less than 2,000, the solubility of the polymer compound in a solvent becomes particularly high, and hence the concentration of the polymer compound in the composition for a coating can be increased. Therefore, the flexibility and the heat resistance of the coating film can be improved. The weight-average molecular weight of the polymer compound is determined by the measurement method defined as above.

The concentration of the aforementioned polymer compound (other than the polymer compound (A)) in the composition for a coating is not particularly limited, but is preferably 0% to 20% by mass and more preferably 0% b to 10% by mass. For example, when an insulating film is formed using the composition for a coating, excellent characteristics can be imparted to the film. One kind of the polymer compound may be used, or two or more kinds thereof may be used by being mixed together.

The epoxy resin is not particularly limited as long as it is a compound having oxirane or oxetane, but is preferably a compound having two or more oxirane rings. Examples of the epoxy resin include a bisphenol A-type epoxy resin, a glycidyl ester-type epoxy resin, an alicyclic epoxy resin, a polymer of oxirane-containing monomer, and a copolymer of an oxirane-containing monomer and other monomers.

Specific examples of the oxirane-containing monomer include glycidyl (meth)acrylate, 3,4-epoxycyclohexyl (meth)acrylate, and methyl glycidyl (meth)acrylate.

Specific examples of other monomers to be copolymerized with the oxirane-containing monomer include (meth) acrylic acid, methyl (meth)acrylate, ethyl (meth)acrylate, isopropyl (meth)acrylate, n-butyl (meth)acrylate, iso-butyl (meth)acrylate, tert-butyl (meth)acrylate, cyclohexyl (meth) acrylate, benzyl (meth)acrylate, 2-hydroxyethyl (meth)acrylate, 2-hydroxypropyl (meth)acrylate, styrene, methyl styrene, chloromethyl styrene, (3-ethyl-3-oxetanyl) methyl (meth)acrylate, N-cyclohexylmaleimide, and N-phenylmaleimide.

The concentration of the epoxy resin in the composition for a coating is not particularly limited, but is preferably 0% to 20% by mass and more preferably 0% to 10% by mass. In a case where the concentration is within the above range, the heat resistance, chemical resistance, and flatness of the film formed of the composition for a coating of the present invention become excellent. One kind of the epoxy resin may be used, or two or more kinds thereof may be used by being mixed together.

The acryl resin is not particularly limited as long as it is a resin having an acryl group or a methacryl group. Examples of the acryl resin include a monofunctional polymerizable monomer having a hydroxyl group, a monofunctional polymerizable monomer which does not having a hydroxyl group, a homopolymer of bifunctional (meth) acrylate or polyfunctional (meth)acrylate having 3 or more functional groups, and a copolymer of these monomers.

Specific examples of the monofunctional polymerizable monomer having a hydroxyl group include 2-hydroxyethyl (meth)acrylate, 2-hydroxypropyl (meth)acrylate, 4-hydroxybutyl (meth)acrylate, and 1,4-cyclohexanedimethanol mono(meth)acrylate. Among these, 4-hydroxybutyl acrylate and 1,4-cyclohexanedimethanol monoacrylate are preferable because these can make the formed film flexible.

Specific examples of the monofunctional polymerizable monomer which does not have a hydroxyl group include glycidyl (meth)acrylate, 3,4-epoxycyclohexyl (meth)acrylate, methyl glycidyl (meth)acrylate, 3-methyl-3-(meth) acryloxymethyl oxetane, 3-ethyl-3-(meth)acryloxymethyl oxetane, 3-methyl-3-(meth)acryloxyethyl oxetane, 3-ethyl-3-(meth)acryloxyethyl oxetane, p-vinylphenyl-3-ethyloxeta-3-ylmethyl ether, 2-phenyl-3-(meth)acryloxymethyl oxetane. 2-trichloromethyl-3-(meth)acryloxymethyl oxetane, 4-trifluoromethyl-2-(meth)acryloxymethyl oxetane, (meth)acrylic acid, methyl (meth)acrylate, ethyl (meth)acrylate, isopropyl (meth)acrylate, butyl (meth)acrylate, isobutyl (meth)acrylate, t-butyl (meth)acrylate, cyclohexyl (meth)acrylate, benzyl (meth)acrylate, styrene, methyl styrene, chloromethyl styrene. (3-ethyl-3-oxetanyl)methyl (meth)acrylate, N-cyclohexylmaleimide, N-phenylmaleimide, vinyl toluene, (meth)acrylamide, tricyclo[5.2.1.$0^{2,6}$]decanyl (meth)acrylate, dicyclopentenyloxyethyl (meth)acrylate, isobornyl (meth)acrylate, phenyl (meth)acrylate, glycerol mono(meth)acrylate, a polystyrene macromonomer, a polymethyl methacrylate macromonomer, N-acryloylmorpholine, 5-tetrahydrofurfuryloxycarbonyl pentyl (meth)acrylate, (meth)acrylate of an ethylene oxide adduct of lauryl alcohol, (meth)acrylic acid, crotonic acid, α-chloroacrylic aid, cinnamic acid, maleic acid, fumaric acid, itaconic acid, citraconic acid, mesaconic acid, ω-carboxy-polycaprolactone mono(meth)acrylate, mono[2-(meth)acryloyloxyethyl]succinate, mono[2-(meth)acryloyloxyethyl] maleate, and mono[2-(meth)acryloyloxyethyl]cyclohexene-3,4-dicarboxylate.

Specific examples of the bifunctional (meth)acrylate include bisphenol F ethylene oxide-modified di(meth)acrylate, bisphenol A ethylene oxide-modified di(meth)acrylate, isocyanuric acid ethylene oxide-modified di(meth)acrylate, polyethylene glycol di(meth)acrylate, polypropylene glycol di(meth)acrylate, pentaerythritol di(meth)acrylate, pentaerythritol di(meth)acrylate monostearate. 1,4-butanediol di(meth)acrylate, 1,6-hexanediol di(meth)acrylate, 1,9-nonanediol di(meth)acrylate, 1,4-cyclohexanedimethanol di(meth)acrylate, 2-n-butyl-2-ethyl-1,3-propanediol di(meth)acrylate, trimethylolpropane di(meth)acrylate, and dipentaerythritol di(meth)acrylate.

Specific examples of the polyfunctional (meth)acrylate having 3 or more functional groups include trimethylolpropane tri(meth)acrylate, ethylene oxide-modified trimethylolpropane tri(meth)acrylate, propylene oxide-modified trimethylolpropane tri(meth)acrylate, epichlorohydrin-modified trimethylolpropane tri(meth)acrylate, ditrimethylolpropane tetra(meth)acrylate, glycerol tri(meth)acrylate, epichlorohydrin-modified glycerol tri(meth)acrylate, diglycerin tetra(meth)acrylate, pentaerythritol tri(meth)acrylate, pentaerythritol tetra(meth)acrylate, dipentaerythritol penta(meth) acrylate, alkyl-modified dipentaerythritol penta(meth) acrylate, alkyl-modified dipentaerythritol tetra(meth) acrylate, alkyl-modified dipentaerythritol tri(meth)acrylate, dipentaerythritol hexa(meth)acrylate, caprolactone-modified dipentaerythritol hexa(meth)acrylate, ethylene oxide-modified phosphoric acid tri(meth)acrylate, tris[(meth)acryloxyethyl]isocyanurate, caprolactone-modified tris[(meth) acryloxyethyl]isocyanurate, and urethane (meth)acrylate.

The concentration of the acryl resin in the composition for a coating of the present invention is not particularly limited, but is preferably 0% to 20% by mass and more preferably 0% to 10% by mass. In a case where the concentration is within the above range, the heat resistance, chemical resistance, and flatness of the coating film formed of the composition for a coating of the present invention become excellent. One kind of the acryl resin may be used, or two or more kinds thereof may be used by being mixed together.

In order to improve the wettability of the composition for a coating with respect to the base substrate and the levelability and the coating properties of the composition for a coating, a surfactant can be used. The concentration of the surfactant is preferably 0% to 1% by mass in 100% by mass of the composition for a coating.

Examples of the surfactant include silicon-based surfactants such as “Byk-300”, “Byk-306”, “Byk-335”, “Byk-310”, “Byk-341”. “Byk-344”, and “Byk-370” (trade names, manufactured by BYK-Chemie GmbH): acryl-based surfactants such as “Byk-354”, “Byk-358”, and “Byk-361” (trade names, manufactured by BYK-Chemie GmbH): and fluorine-based surfactants such as “DFX-18”, “FTERGENT 250”, and “FTERGENT 251” (trade names, manufactured by NEOS COMPANY LIMITED), because these surfactants can improve the coating properties of the composition for a coating of the present invention. One kind of surfactant may be used, or two or more kinds thereof may be used by being mixed together.

In order to prevent the composition for a coating from being electrically charged, an antistatic agent can be used. The concentration of the antistatic agent is preferably 0% to 1% by mass in 100% by mass of the composition for a coating of the present invention.

The antistatic agent is not particularly limited, and any antistatic agent can be used. Specific examples thereof include metal oxides such as tin oxide, a composite oxide of tin oxide-antimony oxide, and a composite oxide of tin oxide-indium oxide and a quaternary ammonium salt. One kind of the antistatic agent may be used, or two or more kinds thereof may be used by being mixed together.

The coupling agent is not particularly limited, and any coupling agent can be used. The concentration of the coupling agent is preferably 0% to 3% by mass in 100% by mass of the composition for a coating of the present invention.

As the coupling agent, a silane coupling agent is preferable. Specific examples of the silane coupling agent include a trialkoxysilane compound, a dialkoxysilane compound, and the like. One kind of the silane coupling agent may be used, or two or more kinds thereof may be used by being mixed together.

The epoxy curing agent is not particularly limited, and any epoxy curing agent can be used. The concentration of the epoxy curing agent is preferably 0% to 5% by mass in 100% by mass of the composition for a coating of the present invention.

Specific examples of the epoxy curing agent include an organic acid dihydrazide compound, imidazole and a derivative thereof, dicyandiamide, aromatic amine, polyvalent carboxylic acid, polyvalent carboxylic anhydride, and the like. One kind of the epoxy curing agent may be used, or two or more kinds thereof may be used by being mixed together.

The wettability enhancer can improve the wettability of the composition with respect to the base material and can improve the uniformity of the film to be formed. Examples of the wettability enhancer include an acryl-based copolymer, a polyoxyethylene fatty acid ester-based compound, and the like. Among these, the acryl-based copolymer is preferable, because it can improve the transparency, scratch resistance, and solvent resistance of the film. The content of the wettability enhancer as a solid is not particularly limited. The upper limit of the content of the wettability enhancer in the composition for a coating is preferably equal to or less than 70% by mass, and more preferably equal to or less than 40% by mass. The lower limit thereof is preferably equal to or higher than 4% by mass. One kind of the wettability enhancer may be used, or two or more kinds thereof may be used by being mixed together.

By mixing the defoamer with the composition for a coating, foams can be effectively removed, and the formation of foams in the composition can be inhibited. Examples of the defoamer include a glycol-based compound such as polyacetylene glycol, a siloxane-based compound such as organic modified polysiloxane, an emulsion obtained by dispersing polydimethyl siloxane in water by using an emulsifier, and the like. Among these, the polydimethyl siloxane emulsion is preferable because the emulsion has excellent defoaming properties. The content of the defoamer is not particularly limited, but is preferably 1% to 30% by mass in the composition for a coating. One kind of the defoamer may be used, or two or more kinds thereof may be used by being mixed together.

The composition for a coating may contain a binder resin. By adding the binder resin to the composition, the film formability, the flexibility and adhesiveness of the film, the printing properties, and the adhesiveness of prints are improved in some cases. Examples of the binder resin include homopolymers such as polyester, poly(meth)acrylate, polyurethane, polyvinyl acetate, polyvinylidene chloride, polyamide, polyimide, polyvinyl alcohol, polyacryl polyol, and polyester polyol; copolymers containing, as a copolymerization component, a compound selected from the group consisting of styrene, vinylidene chloride, vinyl chloride, and alkyl (meth)acrylate; and the like.

The content of the binder resin is not particularly limited, but is preferably equal to or less than 60%/o by mass and more preferably equal to or less than 40% by mass in the composition for a coating. One kind of the binder resin may be used, or two or more kinds thereof may be used by being mixed together.

The composition for a coating may contain a silane coupling agent. Examples of the silane coupling agent include 3-glycidoxypropyltrimethoxysilane, 3-glycidoxypropylmethyldimethoxysilane, 2-(3,4-epoxycyclohexyl)ethyltrimethoxysilane, 3-mercaptotrimethoxysilane, and the like. The content of the silane coupling agent is not particularly limited, but is preferably equal to or less than 50% by mass in the composition for a coating. One kind of the silane coupling agent may be used, or two or more kinds thereof may be used by being mixed together.

The composition for a coating may contain a thickener for the purpose of improving the viscosity of the composition. Examples of the thickener include water-soluble polymers such as a salt and a derivative of alginic acid, a xanthan gum derivative, a water-soluble polymer of a saccharide compound such as carrageenan or cellulose, and the like. The content of the thickener is not particularly limited, but is preferably equal to or less than 50% by mass in the composition for a coating. One kind of the thickener may be used, or two or more kinds thereof may be used by being mixed together.

The composition for a coating may contain a particle material such as colloidal silica, hollow silica, fluororesin fine particles, or fine particles of metal such as titanium. The content of the fine particle material is not particularly limited, but is preferably equal to or less than 50% by mass in the composition for a coating. One kind of the fine particle material may be used, or two or more kinds thereof may be used by being mixed together.

The composition for a coating may contain an organic carboxylic acid having a carboxyl group. The organic carboxylic acid includes monovalent and polyvalent aliphatic and aromatic carboxylic acids, and may contain functional groups such as a hydroxyl group and/or a vinyl group in a molecule. Examples of the aliphatic carboxylic acid include acetic acid, butyric acid, hexane carboxylic acid, octane carboxylic acid, acetoacetate, malonic acid, succinic acid, glutaric acid, adipic acid, fumaric acid, maleic acid, malic acid, tartaric acid, citric acid, and the like. Examples of the aromatic carboxylic acid include benzoic acid, salicylic acid, gallic acid, cinnamic acid, phthalic acid, trimellitic acid, pyromellitic acid, and the like.

In the composition for a coating, water or an organic solvent may be used as a medium, but it is preferable to use an organic solvent. The number of carbon atoms in the organic solvent is preferably 1 to 12, and more preferably 1 to 6. Examples of the organic solvent include solvents containing ethyl lactate, ethanol, hexafluoroisopropanol, ethylene glycol, propylene glycol, glycerin, diethylene glycol dimethyl ether, diethylene glycol diethyl ether, diethylene glycol methyl ethyl ether, diethylene glycol monoethyl ether acetate, ethylene glycol monobutyl ether, ethylene glycol monoethyl ether acetate, propylene glycol monomethyl ether acetate, methyl 3-methoxypropionate, ethyl 3-ethoxypropionate, cyclohexanone, 1,3-dioxolane, ethylene glycol dimethyl ether, 1,4-dioxane, propylene glycol dimethyl ether, propylene glycol monomethyl ether, ethylene glycol monomethyl ether, ethylene glycol monomethyl ether acetate, anisole, ethyl lactate, dipropylene glycol dimethyl ether, diethylene glycol isopropyl methyl ether, dipropylene glycol monomethyl ether, diethylene glycol diethyl ether, diethylene glycol monomethyl ether, diethylene glycol butyl methyl ether, tripropylene glycol dimethyl ether, triethylene glycol dimethyl ether, diethylene glycol monobutyl ether, ethylene glycol monophenyl ether, triethylene glycol monomethyl ether, diethylene glycol dibutyl ether, propylene glycol monobutyl ether (1-butoxy-2-propanol), propylene glycol monoethyl ether (l-ethoxy-2-propanol), propylene glycol monomethyl ether (1-methoxy-2-propanol), triethylene glycol divinyl ether, tripropylene glycol monomethyl ether, tetramethylene glycol monovinyl ether, methyl benzoate, ethyl benzoate, 1-vinyl-2-pyrrolidone, 1-butyl-2-pyrrolidone, 1-ethyl-2-pyrrolidone, 1-(2-hydroxyethyl)-2-pyrrolidone, 2-pyrrolidone, 1-methyl-2-pyrrolidone, 1-acetyl-2-pyrrolidone, N,N-diethylacetamide, N,N-dimethylpropionamide, N-methyl-ε-caprolactam, 1,3-dimethyl-2-imidazolidinone, γ-butyrolactone, tetraethoxysilane, tetrapropoxysilane, tetrabutoxysilane, methyl trimethoxysilane, methyl triethoxysilane, dimethyl dimethoxysilane, dimethyl diethoxysilane, diphenyl dimethoxysilane, and diphenyl diethoxysilane.

Among these, alcohol compounds (preferably having 1 to 12 carbon atoms and more preferably having 1 to 6 carbon atoms) such as methanol, ethanol, and hexafluoroisopropanol are preferable.

One kind of the organic solvent may be used, or two or more kinds thereof may be used by being mixed together.

The method for coating a base material with the composition for a coating is not particularly limited, and can be appropriately selected from the methods widely used in the related art. Examples of the method include coating methods such as spin coating, gravure coating, bar coating, dip coating, curtain coating, die coating, and spray coating. Furthermore, by adopting a printing method such as screen printing, spray printing, ink jet printing, relief printing, intaglio printing, or planographic printing, a base material may be coated with the composition.

The thickness of a coating (cured film) is not particularly limited, and can be appropriately selected according to the purpose. From the viewpoint of coating costs, the film thickness calculated after heating and drying is preferably equal to or less than 100 μm, and more preferably 0.5 to 50 μm.

The composition for a coating of the present invention and the coating formed of the composition may be colored or colorless. Here, it is preferable that the coating is a transparent film because then the effects of the present invention are more markedly exhibited.

Examples of the substrate which can be used in the present invention include a glass epoxy substrate, a glass composite substrate, a paper phenol substrate, a paper epoxy substrate, a green epoxy substrate, and a BT resin substrate that meet various standards such as FR-1, FR-3, FR-4, CEM-3, and E668. Although the base material used in the present invention is described using a substrate for example, the base material is not limited to a plate-like substance (substrate), and a wide variety of materials to be coated can also be used. The base material may be, for example, an atypical substance such as the surface of a building material (wall) or outer surfaces of electronic substrates.

Examples of other usable base materials (such as a substrate) include a substrate formed of a metal such as copper, brass, phosphor bronze, beryllium copper, aluminum, gold, silver, nickel, tin, chromium, or stainless steel (a substrate having these metals on the surface thereof may also be used); a substrate formed of ceramics such as aluminum oxide (alumina), aluminum nitride, zirconium oxide (zirconia), silicate of zirconium (zircon), magnesium oxide (magnesia), aluminum titanate, barium titanate, lead titanate (PT), lead zirconate titanate (PZT), lead lanthanum zirconate titanate (PLZT), lithium niobate, lithium tantalate, cadmium sulfide, molybdenum sulfide, beryllium oxide (beryllia), silicon oxide (silica), silicon carbide, silicon nitride, boron nitride, zinc oxide, mullite, ferrite, steatite, forsterite, spinel, or spodumene (a substrate having these ceramics on the surface thereof may also be used): a substrate formed of a resin such as a polyethylene terephthalate (PET) resin, a polybutylene terephthalate (PBT) resin, a polycyclohexylenedimethylene terephthalate (PCT) resin, a polyphenylene sulfide (PPS) resin, a polycarbonate resin, a polyacetal resin, a polyphenylene ether resin, a polyamide resin, a polyarylate resin, a polysulfone resin, a polyether sulfone resin, a polyether imide resin, a polyamide imide resin, an epoxy resin, an acryl resin, TEFLON (registered trademark), a thermoplastic elastomer, or a liquid crystal polymer (a substrate having these resins on the surface thereof may also be used); a semiconductor substrate such as silicon, germanium, or gallium arsenide: a glass substrate: a substrate having an electrode material, such as tin oxide, zinc oxide, ITO, or ATO, formed on the surface thereof; and a gel sheet such as α GEL, β GEL, θ GEL, or γ GEL (registered trademarks, manufactured by Taica Corporation).

The composition for polymerization of the present invention can be used in various materials. For example, the composition for polymerization can be used in ink, coatings, paints, films, adhesives, pressure sensitive adhesives, detergents, paper additives, cosmetic materials, semiconductor materials, functional gel, and recording materials, or used for functionalizing fiber or molded articles formed of a resin.

More specifically, examples of the ink include the ink jet ink described in JP2010-106085A or the like and the ink for wiring utensils described in JP2008-10175A or the like. Examples of the coating include the coating for medical products described in JP2011-072341A or the like, the coating for biochemical assay described in JP2007-225574A or the like, the antifouling coating described in JP2010-095707A or the like, the coating for building materials described in JP2011-088995A or the like, and the sealant for electronic instruments described in JP2012-000828A or the like. Examples of the paints include the versatile paint described in JP1986-275367A (JP-S61-275367A) or the like and the self-repairing paint described in JP2013-049839A or the like. Examples of the films include the hardcoat film described in JP2013-075955A or the like, the optical film described in JP2012-098526A or the like, the solar cell back sheet described in JP2012-227382A or the like, and the heat shielding film described in JP2012-128231A or the like. Examples of the adhesives include the dental adhesive described in JP2010-235458A or the like, the medical adhesive described in JP2011-026551A or the like, and the adhesive for recording media described in JP2011-198434A or the like. Examples of the pressure sensitive adhesives include the pressure sensitive adhesive for optical members described in WO10/092988A or the like and the pressure sensitive adhesive for hardcoat films described in JP2013-032500A or the like. Examples of the detergents include the detergent for clothes described in JP1998-140183A (JP-H10-140183A) or the like and the detergent for skin described in JP2005-179303A or the like. Examples of the paper additives include the additive for making paper described in JP2008-174897A or the like and the coating agent for recording paper described in JP3892220B or the like. Examples of the cosmetic materials include the granular coating agent described in JP2004-189652A or the like, the gel for cosmetics described in JP2011-241172A or the like, and the humectant described in JP2002-255730A or the like. Examples of the semiconductor materials include the resist underlayer film described in JP2012-203393A or the like and the nanoimprinting material described in JP2012-214022A or the like. Examples of the functional gel include the gel for water treatment described in JP2009-219978A or the like, the gel for civil engineering described in JP1995-242873A (JP-H07-242873A) or the like, the electrolyte gel described in JP2008-285668A or the like, the water absorbing gel described in JP2008-538375A or the like, and the medical gel described in JP2011-197196A or the like. Examples of the recording materials include the hardcoating agent for recording media described in JP2011-126991A or the like and the additives for recording media described in JP1994-318318A (JP-H06-318318A) or the like. Examples of functionalization of fiber or molded materials formed of a resin include the antifouling fiber product described in JP2007-191826A or the like, the hydrophilization of the resin surface described in JP2001-348444A or the like, and the impartation of antistatic properties described in JP1988-58178B (JP-S63-58178B) or the like.

EXAMPLES

Hereinafter, the present invention will be more specifically described based on examples, but the present invention is not limited to the following examples. Unless otherwise specified, the formulation and the amount of components mixed-in represented by using "%" and "part" in the examples are based on mass.

Example 1

[Synthesis of Specific Sulfobetaine Monomer [S]]

By the same method as the synthesis method described in JP2011-245846A, synthesis was performed, thereby obtaining a crystal of 4-sulfonatobutyl[3-(methacryloylamino)propyl]dimethyl ammonium. Specifically, 130 g (0.764 mol) of N-[3-(dimethylamino)propyl]methacrylamide, 104 g of butane sultone, and 234 mg of 4-hydroxy-2,2,6,6-tetramethylpiperidinoxy were dissolved in 380 ml of acetonitrile and heated for 6 hours at 70° C. After the solution was cooled, 1,350 ml of acetone and 150 ml of methanol were added thereto, followed by stirring for 1 hour at room temperature (about 25° C.). The precipitated crystal was filtered and washed thoroughly with acetone, thereby obtaining 200.0 g of 4-sulfonatobutyl[3-(methacryloylamino)propyl]dimethyl ammonium (sample cS1).

5.0 g of the crystal cS1 was dissolved and recrystallized under the respective conditions described in the following Table 1. Specifically, methanol or water was used as a good solvent, acetonitrile was used as a poor solvent, and the recrystallization was performed according to the flowchart shown in FIG. 1. At the time of reaction and recrystallization, all of the operations were performed in a gas purge-type glove box under a nitrogen stream.

TABLE 1

| Sample No. | Good solvent (50 mL) | Poor solvent (500 mL) | Moisture content |
|---|---|---|---|
| cS1 | N/A | N/A | 1.30% |
| S1 | MeOH/water = 99.75/0.25 | Acetonitrile (drying) | 3.10% |
| S2 | MeOH/water = 99.5/0.5 | Acetonitrile (drying) | 4.30% |
| S3 | MeOH/water = 99/1 | Acetonitrile (drying) | 4.60% |
| S4 | MeOH/water = 98.5/1.5 | Acetonitrile (drying) | 5.50% |
| S5 | MeOH/water = 98/2 | Acetonitrile (drying) | 6.20% |
| S6 | MeOH/water = 96/4 | Acetonitrile (drying) | 7.90% |
| S7 | MeOH/water = 92/8 | Acetonitrile (drying) | 9.10% |
| S8 | MeOH/water = 91/9 | Acetonitrile (drying) | 9.80% |
| cS2 | MeOH/water = 90/10 | Acetonitrile (drying) | 10.40% |

<Note for table>

MeOH: methanol

MeOH/water . . . ratio between methanol and water (based on mass)

Moisture content: amount of moisture contained in the powder of a specific sulfobetaine monomer (content rate: based on mass)

<Moisture Content>

By using a Karl Fischer titration device (coulometric titration-type moisture content measurement device of CA-06 model manufactured by Mitsubishi Chemical Corporation), the amount of moisture (mg) in the sample obtained after recrystallization was measured, and the moisture content (%) in the sample was calculated by the following Equation (A).

Moisture content (%)=[amount of moisture (mg)/measurement sample (mg)]×100 Equation (A)

The detailed conditions for the measurement were based on JIS K 0113:2005.

<Evaluation of Storage Stability at High Temperature>

100 mg of each sample powder was weighed and exposed to an environment with a temperature of 70° C. and a humidity of 30% for 48 hours. Then, the purity of the sample powder was measured by HPLC. The measurement conditions are shown below.

TABLE 2

| Test No. | Sample No. | Purity A | Purity B | Amount of change (A − B) |
|---|---|---|---|---|
| c101 | cS1 | 99.6% | 96.2% | 3.4% |
| 101 | S1 | 99.7% | 98.9% | 0.8% |
| 102 | S2 | 99.7% | 99.3% | 0.4% |
| 103 | S3 | 99.7% | 99.4% | 0.3% |
| 104 | S4 | 99.6% | 99.5% | 0.1% |
| 105 | S5 | 99.6% | 99.4% | 0.2% |
| 106 | S6 | 99.5% | 98.9% | 0.6% |
| 107 | S7 | 99.7% | 99.0% | 0.7% |
| 108 | S8 | 99.7% | 98.6% | 1.1% |
| c102 | cS2 | 99.6% | 97.0% | 2.6% |

<Note for table>

Purity A: purity before evaluating storage stability

Purity B: purity after evaluating storage stability

<Purity>

The purity of the specific sulfobetaine monomer was measured by the following method.

100 mg of the original sample was weighed, and 100 mL of deionized water was added thereto such that the sample dissolved, thereby obtaining a sample solution. 2 μl of the sample solution was measured by liquid chromatography under the following conditions. By an automatic integration method, the percentage of a peak surface area of each peak was determined, and the percentage of a peak surface area of the main peak was taken as the purity (HPLC). Here, the peak resulting from the injection is excluded from the calculation.

Condition

Column: Mightysil RP-18 GP (4.6 mm×250 mm)

Column temperature: 40° C.

Mobile phase: mixed liquid of 100 mL of methanol/900 mL of deionized water/1.8 mL of phosphoric acid/1.8 mL of triethylamine Flow rate: adjusted such that the main peak appeared within about 5 minutes and the raw material 3,3'-dimethylaminopropyl methacrylamide was eluted within about 4 minutes (reference: 1.0 mL/min)

Detection wavelength: 210 nm

Range of area measurement: for 10 minutes from the beginning of measurement

As is evident from the above results, the powder of the specific sulfobetaine monomer in which the amount of moisture was within a specific range was inhibited from being decomposed even after the powder was stored at a high temperature (70° C.) for 48 hours, and maintained high purity.

Example 2

<Evaluation of Composition for Coating>

The powder having undergone the stability evaluation described above was made into a coating film by the following method.

In Table 2, the powder (4.5 g) having undergone the storage evaluation, 2-hydroxyethyl methacrylate (manufactured by Wako Pure Chemical Industries, Ltd., 4.5 g), triethylene glycol dimethacrylate (manufactured by Wako Pure Chemical Industries, Ltd., 0.8 g), and Irgacure 2959 (manufactured by BASF SE, 0.2 g), and methanol (3.3 g) were mixed together, thereby preparing a photocurable composition. By using a spin coater, a 24 mm×24 mm glass substrate was coated with the obtained photocurable composition for 20 seconds under the condition of 2,000 rpm. Then, the glass substrate of the coated surface was irradiated with black light for 5 minutes, thereby preparing a glass substrate on which a coating film of a photocurable material was formed. The thickness of the coating film was 0.9 μm.

The molecular weight of the polymer using the sample of the Test No. 101 was measured. As a result, it was confirmed that the polymer has a weight-average molecular weight of 15,900.

The substrate was left in the atmosphere for 1 week at room temperature (about 25° C.), and the degree of coloring of the coating film at that time was judged based on the following standards.

The absorbance (relative value obtained in a case where the absorbance of only the glass substrate was regarded as being 100) at a wavelength of 400 nm was measured using an ultraviolet-visible spectrophotometer (manufactured by Shimadzu Corporation, UV-2550 [trade name]). The absorbance was measured at room temperature (25° C.).

AA: equal to or higher than 97

A: equal to or higher than 95 and less than 97

B: equal to or higher than 90 and less than 95

C: equal to or higher than 80 and less than 90

D: less than 80

TABLE 3

| Test No. | Powder sample | Degree of coloration |
|---|---|---|
| c201 | cS1 | D |
| 201 | S1 | B |
| 202 | S2 | A |
| 203 | S3 | AA |
| 204 | S4 | AA |
| 205 | S5 | A |
| 206 | S6 | A |
| 207 | S7 | A |
| 208 | S8 | B |
| c202 | cS2 | C |

From the above results, it is understood that, in the powder of the specific sulfobetaine monomer in which the amount of moisture is within a specific range, even when a film (coating) of the polymer was formed by using the sample having been stored at a high temperature, a film of good quality that is not colored can be obtained.

The same polymerization reaction as described above was performed by changing the solvent used for the polymerization reaction performed for evaluating the composition for a coating from methanol to water, hexafluoroisopropanol, and the like. As a result, it was confirmed that an excellent coating film can be obtained.

Example 3

[Synthesis of Specific Sulfobetaine Monomer [T]]

195.2 g of 4-sulfonatobutyl[3-(acryloylamino)propyl]dimethyl ammonium (sample cT1) was obtained in the same manner as described above, except that N-[3-(dimethylamino)propyl]methacrylamide used for the synthesis of the specific sulfobetaine monomer [S] was changed to N-[3-(dimethylamino)propyl]acrylamide.

5.0 g of the crystal of the sulfobetaine monomer cT1 was dissolved and recrystallized under the same conditions as in Example 1, thereby obtaining each sample shown in the following Table 4. Table 4 also shows the moisture content measured from each sample.

TABLE 4

| Sample No. | Good solvent (50 mL) | Poor solvent (500 mL) | Moisture content |
|---|---|---|---|
| cT1 | N/A | N/A | 1.20% |
| T1 | MeOH/water = 99.75/0.25 | Acetonitrile (drying) | 3.20% |
| T2 | MeOH/water = 99.5/0.5 | Acetonitrile (drying) | 3.90% |
| T3 | MeOH/water = 99/1 | Acetonitrile (drying) | 4.60% |
| T4 | MeOH/water = 98.5/1.5 | Acetonitrile (drying) | 5.40% |
| T5 | MeOH/water = 98/2 | Acetonitrile (drying) | 6.50% |
| T6 | MeOH/water = 96/4 | Acetonitrile (drying) | 8.00% |
| T7 | MeOH/water = 92/8 | Acetonitrile (drying) | 8.90% |
| T8 | MeOH/water = 91/9 | Acetonitrile (drying) | 9.70% |
| cT2 | MeOH/water = 90/10 | Acetonitrile (drying) | 10.20% |

The abbreviation in the table has the same definition as the abbreviation in Table 1.

Each sample obtained as above was evaluated regarding the storage stability at a high temperature in the same manner as in Example 1. The results are shown in the following Table 5. The purity A is the purity before the evaluation of storage stability, and the purity B is the purity after the evaluation of storage stability.

TABLE 5

| Test No. | Sample No. | Purity A | Purity B | Amount of change (A − B) |
|---|---|---|---|---|
| c301 | cT1 | 99.5% | 95.6% | 3.9% |
| 301 | T1 | 99.5% | 98.9% | 0.7% |
| 302 | T2 | 99.6% | 99.3% | 0.3% |
| 303 | T3 | 99.7% | 99.4% | 0.3% |
| 304 | T4 | 99.6% | 99.5% | 0.1% |
| 305 | T5 | 99.7% | 99.4% | 0.3% |
| 306 | T6 | 99.5% | 98.9% | 0.6% |
| 307 | T7 | 99.4% | 98.6% | 0.8% |
| 308 | T8 | 99.5% | 98.4% | 1.1% |
| c302 | cT2 | 99.4% | 96.7% | 2.7% |

Example 4

By using the samples shown in Table 5 having undergone the storage stability evaluation (purity B), the evaluation of the composition for a coating was performed in the same manner as in Example 2. The evaluation conditions and the evaluation standards were the same as in Example 2. The results are shown in the following Table 6.

TABLE 6

| Test No. | Powder sample | Degree of coloration |
|---|---|---|
| c401 | cT1 | D |
| 401 | T1 | B |
| 402 | T2 | A |
| 403 | T3 | AA |
| 404 | T4 | AA |
| 405 | T5 | A |
| 406 | T6 | A |
| 407 | T7 | A |
| 408 | T8 | B |
| c402 | cT2 | D |

From the above results, it is understood that even with the compound represented by Formula (I) in which R represents a hydrogen atom, it is possible to obtain a film of good quality that is highly stable at the time of being stored at a high temperature and is not colored.

Hitherto, the present invention has been described based on the embodiments of the present invention. However, the inventors of the present invention consider that, unless otherwise specified by the inventors, the present invention is not limited to any detail of the description of the present invention and should be construed in a broad sense without departing from the gist of the present invention shown in the attached claims.

The present application claims priorities based on JP2015-028179 filed in Japan on Feb. 17, 2015 and JP2015-132555 filed in Japan on Jul. 1, 2015, the contents of which are incorporated into the present specification by reference.

What is claimed is:

1. A composition for polymerization, comprising:

a monomer represented by the following Formula (I); and water, wherein a moisture content is equal to or higher than 3% by mass and less than 10% by mass, (I)

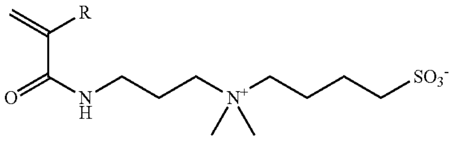

wherein R represents a hydrogen atom or a methyl group.

2. The composition for polymerization according to claim 1, wherein the moisture content is equal to or higher than 4% by mass and less than 9.5% by mass.

3. The composition for polymerization according to claim 1, further comprising:

a monomer having an ethylenically unsaturated group.

4. The composition for polymerization according to claim 1, wherein in the monomers, a content rate of the monomer represented by Formula (I) is equal to or higher than 5% by mass and equal to or less than 90% by mass.

5. The composition for polymerization according to claim 1 that is in a powdered state.

6. The composition for polymerization according to claim 1 that is obtained through steps of synthesizing the monomer represented by Formula (I), then adding the synthesized product to a good solvent, and subsequently mixing the good solvent with a poor solvent such that the monomer represented by Formula (I) is precipitated.

7. A composition for a coating , comprising:
a composition for polymerization in a medium,
wherein the composition for polymerization comprises:
a monomer represented by the following Formula (I), and water,
wherein a moisture content is equal to or higher than 3% by mass and less than 10% by mass, (I)

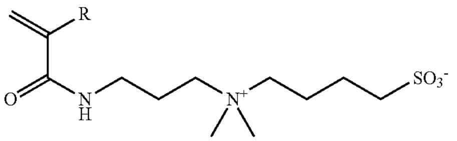

wherein R represents a hydrogen atom or a methyl group, and
wherein the medium is an organic solvent.

8. A method for producing a composition for a coating, comprising:
a step of mixing a composition for polymerization with a medium,
wherein the composition for polymerization contains a monomer represented by the following Formula (I) and water, and
a moisture content in the composition for polymerization is equal to or higher than 3% by mass and less than 10% by mass, (1)

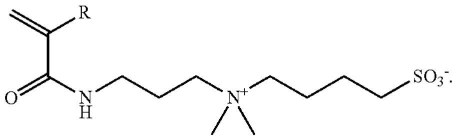

wherein R represents a hydrogen atom or a methyl group.

9. The method for producing a composition for a coating according to claim 8,
wherein the composition for polymerization further contains a monomer having an ethylenically unsaturated group.

10. A method for producing the composition for polymerization according to claim 1 the method, comprising:
a step of synthesizing the monomer represented by Formula (I), then adding the synthesized product to a good solvent, and subsequently mixing the good solvent with a poor solvent such that the monomer represented by Formula (I) is precipitated,
wherein a moisture content to be contained in the good solvent is from 0.25% by mass to 9% by mass.

* * * * *